(12) United States Patent
Kreindel

(10) Patent No.: US 11,925,407 B2
(45) Date of Patent: Mar. 12, 2024

(54) FRACTIONAL TREATMENT OF URINARY INCONTINENCE

(71) Applicant: Inmode Ltd., Shaar Yokneam (IL)

(72) Inventor: Michael Kreindel, Richmond Hill (CA)

(73) Assignee: Inmode Ltd., Yokneam (IL)

( * ) Notice: Subject to any disclaimer, the term of this patent is extended or adjusted under 35 U.S.C. 154(b) by 371 days.

(21) Appl. No.: 17/110,469

(22) Filed: Dec. 3, 2020

(65) Prior Publication Data

US 2021/0169563 A1 Jun. 10, 2021

Related U.S. Application Data

(60) Provisional application No. 62/943,277, filed on Dec. 4, 2019.

(51) Int. Cl.
| | |
|---|---|
| *A61B 18/14* | (2006.01) |
| *A61B 18/12* | (2006.01) |
| *A61B 18/16* | (2006.01) |
| *A61B 18/00* | (2006.01) |

(52) U.S. Cl.
CPC ...... *A61B 18/1477* (2013.01); *A61B 18/1206* (2013.01); *A61B 18/1485* (2013.01); *A61B 18/16* (2013.01); *A61B 2018/00041* (2013.01); *A61B 2018/00517* (2013.01); *A61B 2018/00577* (2013.01); *A61B 2018/00589* (2013.01); *A61B 2018/00648* (2013.01); *A61B 2018/00791* (2013.01); *A61B 2018/00827* (2013.01); *A61B 2018/00875* (2013.01); *A61B 2018/00892* (2013.01); *A61B 2018/1467* (2013.01)

(58) Field of Classification Search
CPC ............... A61B 17/1477; A61B 17/06; A61B 2018/00517; A61B 2018/1467; A61B 18/1477; A61B 18/16; A61N 1/0514; A61N 1/0521; A61N 1/36007
See application file for complete search history.

(56) References Cited

U.S. PATENT DOCUMENTS

| | | | |
|---|---|---|---|
| 2004/0181214 A1* | 9/2004 | Garabedian | A61B 18/1477 606/41 |
| 2010/0114087 A1* | 5/2010 | Edwards | A61B 8/12 606/33 |

* cited by examiner

*Primary Examiner* — Tammie K Marlen
(74) *Attorney, Agent, or Firm* — Dekel Patent Ltd.; David Klein

(57) ABSTRACT

Apparatus for tissue treatment includes a central blunt urethra fixator, which may serve as a return electrode. An array of electrodes is positioned circumferentially about the central blunt urethra fixator and distanced radially from the central blunt urethra fixator. At least one of the electrodes is an active electrode. The central blunt urethra fixator and electrodes protrude from a housing. A main unit includes an RF generator, a controller unit, a power supply and a user interface. The main unit delivers RF energy between the return electrode and a conductive tip of the active electrode to create collagen contraction in a vicinity of the active electrode.

3 Claims, 5 Drawing Sheets

FRACTIONAL TREATMENT OF URINARY INCONTINENCE

FIELD OF THE INVENTION

The invention relates to a method for fractional treatment of urinary incontinence using radio-frequency (RF) energy delivered through an array of needles.

BACKGROUND OF THE INVENTION

There are many surgical and non-surgical methods for treatment of severe urinary incontinence (SUI) using RF energy. The methods include remodeling of collagenous tissue applying RF energy through a device inserted into the vagina and creating heat to contract the collagenous support tissue.

Some prior art methods create shrinkage of tissue around the bladder neck or urethra. The inventions describe delivering RF energy through the vaginal, urethral or bladder wall.

SUMMARY OF THE INVENTION

The present invention provides a method for fractional treatment of vaginal tissue around the urethra to contract the collagen and/or scar the tissue for better support of the urethral channel. The method includes positioning the device to create fractional lesions at a safe distance from the urethra and vagina. The invention describes a method of treatment of peri-urethral tissue using multiple needles inserted at the introitus into the urethra; the needles are fixed with a member inserted into the urethra.

The device is based on a minimally invasive procedure where at least two needle electrodes are inserted in soft tissue close to the urethra. The size of the electrode is designed to create a higher energy density in the vicinity of the electrode. The RF energy density is high enough to create a contractive tissue change around the electrode. The device has a rigid position fixator designed to be inserted into the urethra and a mechanism for aligning the needle electrodes to be substantially parallel to the urethra so the needles enter the tissue at a predetermined distance from the urethra canal. The purpose of the aligning mechanism is to position the needle electrodes around the urethra to avoid mechanical or thermal damage to the urethra, vagina or bladder wall.

In one embodiment the distance between the urethral position fixator and needle electrodes is fixed. The needle electrode may fill the volume around the urethra to create a stronger thermal effect.

Alternatively, the distance between the needle electrodes and the urethral position fixator can be selected according to the individual anatomy of the patient.

The position fixator may have a smooth surface and a blunt end to avoid mechanical damage of the urethra. Lubrication can be used for easy insertion.

The needle electrodes may be inserted into the tissue to a depth from 3 mm up to 20 mm to provide enough collagen contraction to support the urethra. The active electrode may be rigid enough to avoid undesired bending in the tissue.

The needle electrodes may have an insulated area and a conductive area at the distal end of the electrode. The needle electrodes may have multiple conductive and insulated areas to provide an optimal treatment thermal profile in the tissue. An insulating coating can be used to minimize damage of tissue surface and reduce healing time. Alternatively, the needle electrode may not have an insulating coating.

The needle electrodes may have an embedded temperature sensor to control tissue heating up to the temperature providing collagen contraction. Typically, heating temperature is varied from 45° C. up to 100° C. Temperature can be above 100° C. causing evaporation or carbonization of tissue at high peak RF power. The tissue heating may result in tissue coagulation, tissue ablation, tissue contraction, tissue scarring.

The needle electrode may be inserted manually or by using an electro-mechanical system. Insertion depth can be controlled by the device according to a predetermined setting.

Alternatively, insertion depth can be controlled manually by the user according to depth marks on the device.

The RF energy can be applied to all needles simultaneously or controlled individually for each needle. Energy delivery to the needles can be controlled according to treatment feedback, which can be one or more feedbacks from tissue temperature measurements, tissue impedance or needle position.

The RF energy can be applied between pairs of needles, between groups of needles or between one needle and other needle electrodes acting as a return electrode.

Alternatively, a return electrode can be applied to the tissue surface in the vicinity of the treatment area or to another body part.

The large area fixator inserted into the urethra can serve as a return electrode.

The return electrode should have a substantially larger conductive area than the active electrode to avoid tissue thermal damage in the area coupled to the external electrode. The return electrode can be structured from one or more conductive elements. The return electrode may have an embedded thermal sensor to avoid tissue overheating.

The part of the electrodes coming in contact with the tissue may be made from biocompatible materials. For example, the internal electrode tip may be made from stainless steel or titanium. RF electrodes may have a thin dielectric coating providing capacitive electrical coupling for delivering RF energy.

A motor or solenoid can be used for insertion of the needles into the tissue. Step or DC motor can be used to push the needle electrodes to the predetermined depth. Operation of the motor can be controlled by the controller.

The parameters of the RF energy may be adjusted for tissue contraction. RF energy can be delivered in pulsed or continuous mode. Frequency of RF current may be varied from 200 KHz up to 40 MHz. The most optimal range of RF frequencies used for fractional tissue coagulation is from 400 kHz up to 6 MHz. In order to improve electrical coupling, a conductive solution can be applied to the return electrode. Conductive liquid or gel can be used to hydrate tissue under the return electrode and improve electrical contact. RF energy can be controlled by the controlling of RF power or RF pulse duration. Another option to control average RF power is by delivering constant RF power with a train of shorter pulses and controlling the duty cycle of the RF pulses.

In order to reduce pain and improve tissue conductivity, anesthesia can be applied to the treated tissue prior to the procedure.

Controlling the distance between the active electrode, urethral fixator and return electrode placed in the vagina enables optimizing the safe position of the RF electrode between the urethra and vagina. The distance can be controlled by selection of a treatment tip with a predetermined distance from the fixator to the needles. Alternatively, the fixator position can be adjustable in the same tip to change the distance between the needles and fixator.

In some embodiments the device may have a circuit that measures tissue impedance. Any change in the measured impedance between the electrodes may provide information about the distance between the electrodes. Measuring the tissue impedance also provides information about tissue heating and quality of electrical contact between the return electrode and tissue surface. An electronic circuit may measure RF current, voltage, impedance or other RF parameters.

Cooling of the return electrode and or urethral fixator may reduce risks of side effects.

The system for powering and controlling RF energy delivery may include a power supply that converts AC voltage from the wall plug to stabilized DC voltage. An RF generator may be connected to the power supply and generate high frequency voltage. The RF generator may be designed to maintain constant power in the working range of parameters. The system may have a controller that controls the RF parameters and a user interface includes an LCD screen and touch panel. The controller may have a microprocessor and dedicated software. The monitoring system measures RF parameters including tissue impedance and/or RF current and/or RF voltage or other electronic parameters. The system has one or more connectors to connect one or more electrodes to the system unit.

Thus, in one aspect, the invention provides a method for contracting supporting tissue between urethra and vagina by:
  Inserting a position fixator into the urethra to fix the urethra position.
  Aligning multiple needle electrodes into the tissue around the urethra.
  Applying RF energy between the needle electrodes to heat tissue in the vicinity of the conductive area of the needle electrodes.
  Stopping RF energy delivery when a predetermined amount of energy is reached.
  Extracting the needle electrodes out of the tissue.
  Optionally, rotating the hand piece around the urethra fixator to insert the needle electrodes to the adjacent area.

In another aspect, the invention provides a method for contracting supporting tissue around urethra by:
  Inserting position fixator into the urethra to fix the urethra position.
  Aligning multiple needle electrodes into the tissue around the urethra.
  Applying RF energy between the needle electrodes and the return electrode placed on the tissue surface.
  Stopping RF energy delivery when a predetermined amount of energy is reached.
  Extracting the needle electrodes out of the tissue.
  Optionally, rotating the hand piece around the urethra fixator to insert the needle electrodes to the adjacent area.

Other types of energy include focused ultrasound or laser radiation; they can be used to create fractional lesion around the urethra for treatment of urinary incontinence. Laser energy can be delivered to the tissue surface non-invasively or through the optical fibers inserted into the tissue in the vicinity of the urethra. Focused ultrasound can be used for creating lesions inside the tissue at variable depths. Mechanical multiple small lesions can be created to initiate tissue micro-scarring for better urethral support.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION

Figure 1:
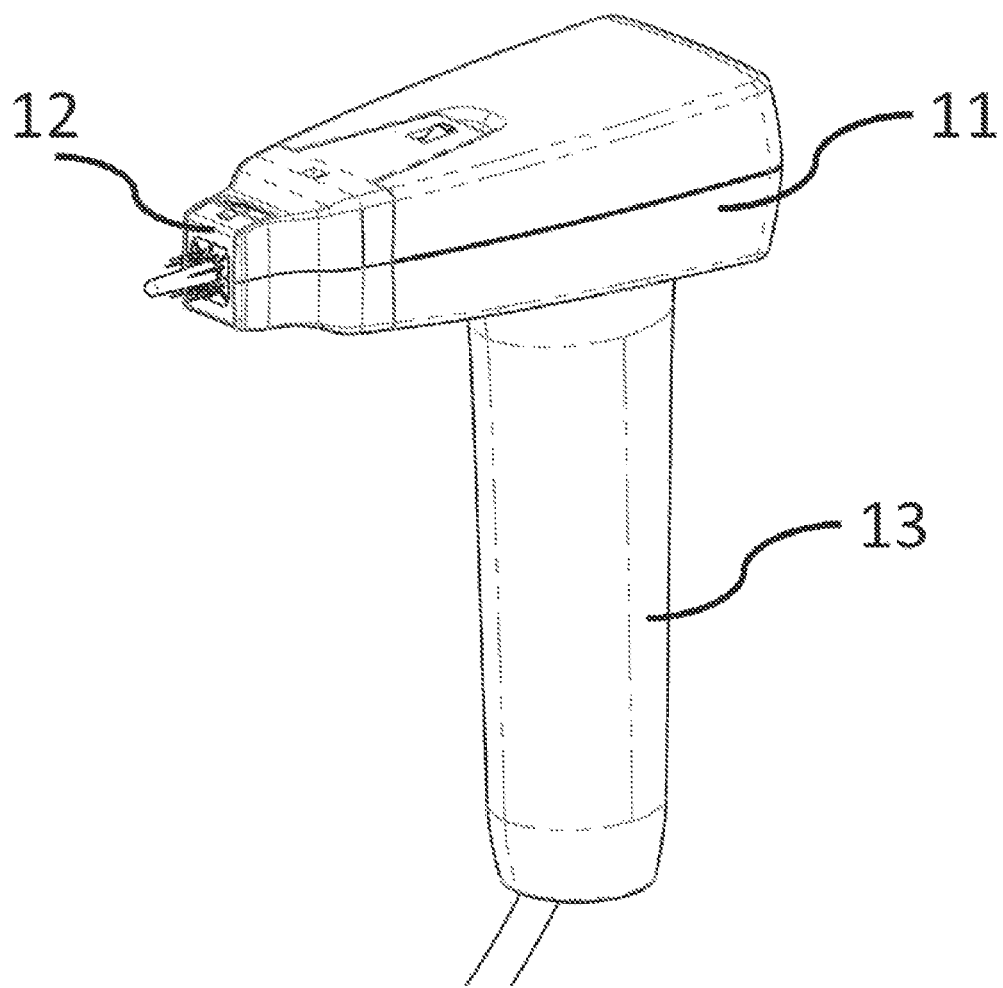
FIG. 1 shows a hand piece design.

FIG. 1 shows a hand piece 11 having a handle 13 and a disposable tip 12 used for applying RF energy to the patient.

Figure 2:
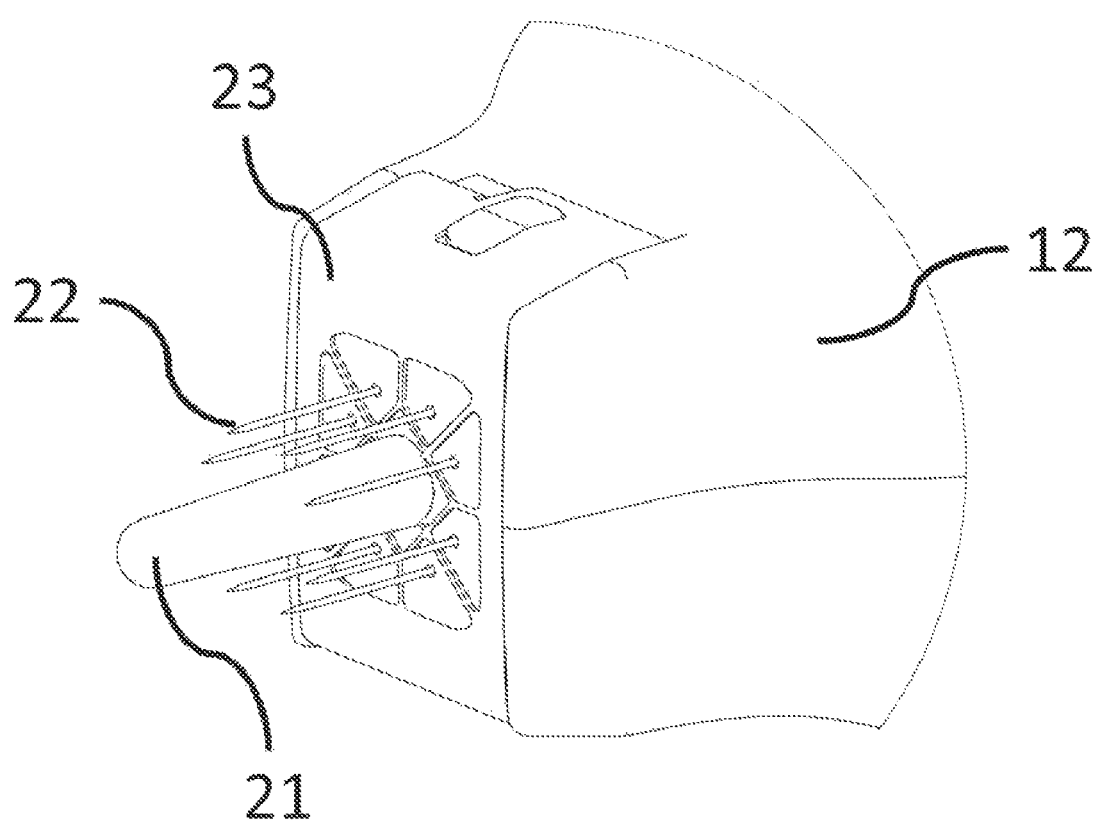
FIG. 2 shows hand piece tips with needle electrodes, return electrode and urethra fixator.

FIG. 2 shows the disposable tip 12 wherein a urethra fixator 21 has a diameter of 3-6 mm. Needle electrodes 22 surround fixator 21 at a distance. This enables creating a thermal lesion around the needles without risk of urethra damage. RF energy is applied between the needle electrodes 22 and return electrode 23 is applied to the tissue surface. The needle electrodes 22 are pushed out of the tip when the user activates the pulse. When the needle electrodes 22 are moved out to a predetermined depth, the pulse of RF energy is applied between the needle electrodes 22 and return electrode 23. Because the conductive area of needle electrodes 22 is smaller than the area of return electrode 23, the thermal effect is stronger around the needles 22.

Figure 3:
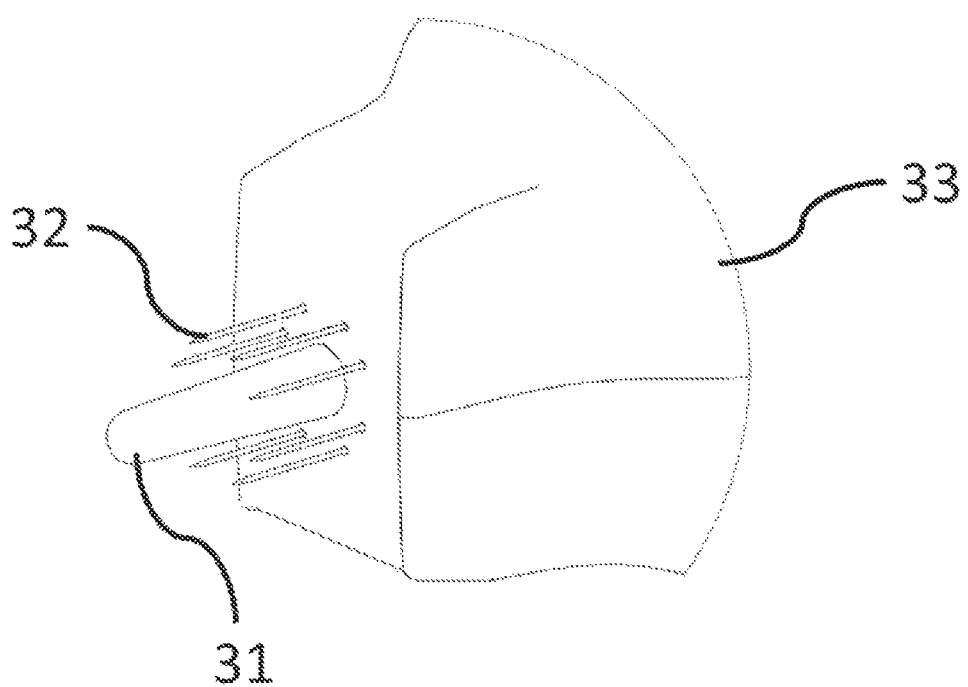
FIG. 3 shows hand piece tips without return electrode.

FIG. 3 shows alternative tips 33 design without an external electrode. The RF energy is applied between one of the needle electrodes 22 acting as an active electrode and other needle electrodes acting as a return electrode. Then RF energy can be switched to connect another needle as the active electrode. Energy is switched between needle electrodes to create a thermal lesion in the vicinity of each lesion.

Alternatively, urethra fixator 31 can be made from a conductive material and act as an return electrode. RF energy is applied between needle electrodes 22 and urethral fixator 31.

Figure 4:
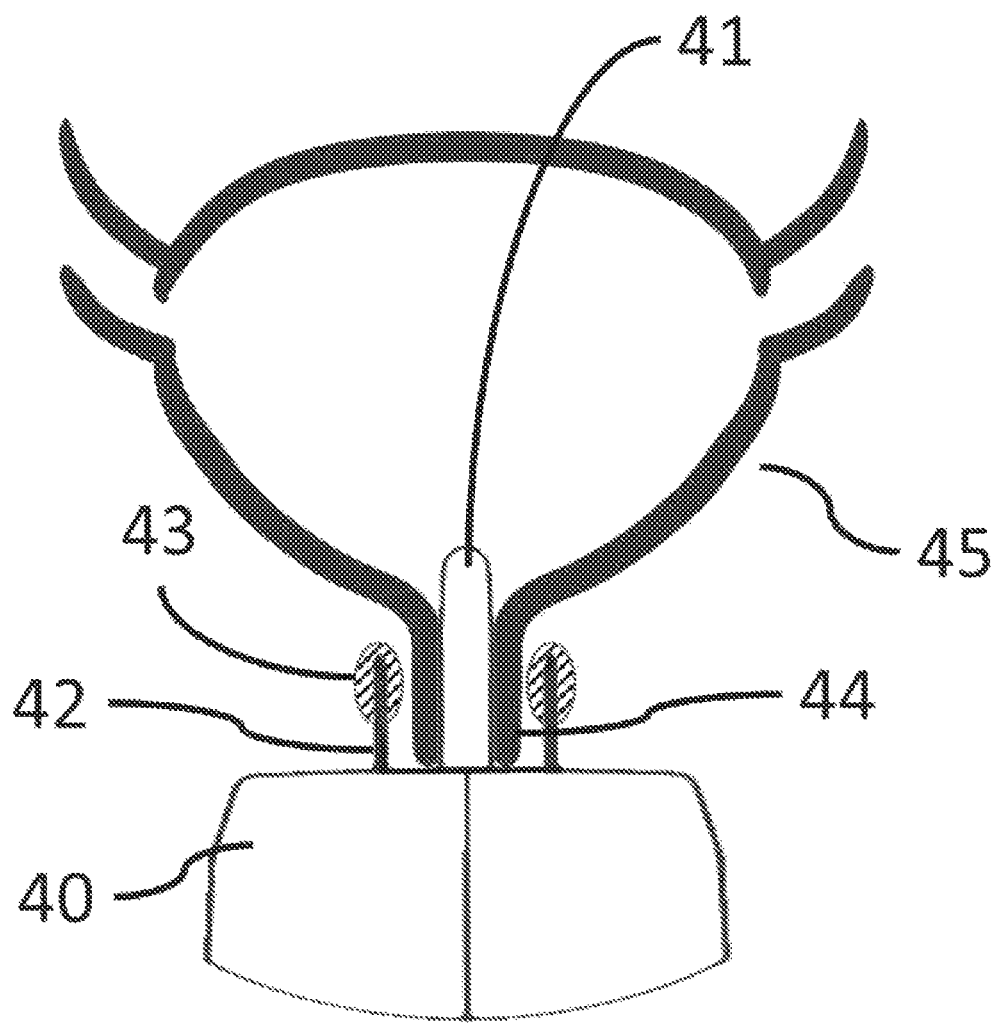
FIG. 4 shows the hand piece tip applied to the urethral tissue.

FIG. 4 demonstrates schematically a disposable tip 40 applied to the tissue. The urethral fixator 41 is inserted into the urethra 44. Needle electrodes 42 are inserted into the tissue around the urethra 44. Depth of needle electrode insertion is limited to avoid damage of the bladder 45. Typically, insertion depth should not exceed 25 mm. RF energy is applied to the needle electrodes 42 to create thermal lesions 43 in vicinity of the needle electrodes. The size of lesions 43 should be small enough to avoid damage of urethra 44. Size of the thermal lesions 43 is controlled by an amount of RF energy applied to the needle electrodes 42 and by duration of RF pulses.

Figure 5A:
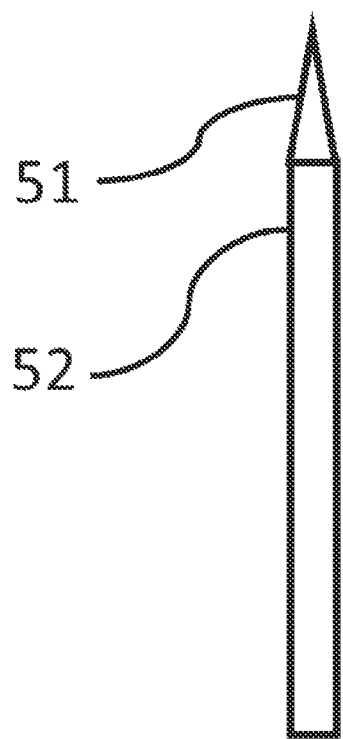
FIG. 5a shows the needle electrode.

The needle electrodes can be made from conductive materials as shown in FIG. 5a to apply RF energy along the entire length of the needle electrode 52 and the sharp end of needle electrode 51.

Figure 5B:
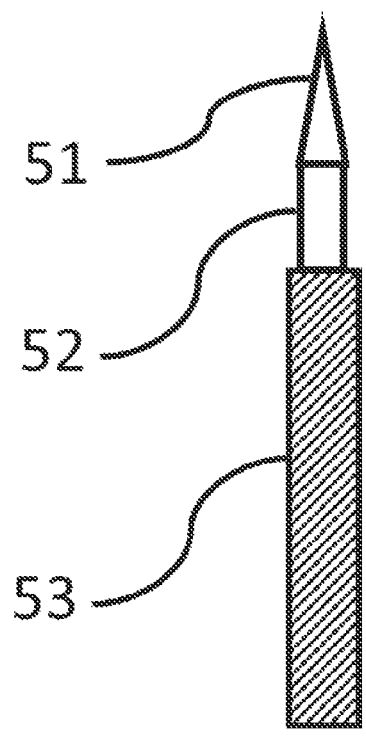
FIG. 5b shows a partially isolated needle electrode.

In order to minimize damage near the tissue surface, the electrode can be partially coated by an insulating material as shown in FIG. 5b. Sharp end 51 and uncoated shaft 52 at the distal end of the needle electrode are uncoated to deliver RF energy. The proximal part 53 of the needle electrode is coated with a thin layer of insulating material to prevent RF energy delivery and minimize damage near the tissue surface.

The method of treatment includes the following steps:

Inserting the fixator 41 into the urethra 43.

Pushing needle electrodes 42 out of the tip into the tissue to predetermined depth.

Applying predetermined amount of RF energy to the needle electrodes 42 to create thermal lesions 43 in vicinity of needle electrodes 42.

Retracting the needle electrodes 42 out of the tissue.

Using the method of the invention to treat urethra supporting tissue, the following exemplary parameter values of RF energy may be used:

RF frequency: 0.2-40 MHz.

Average output RF power: from about 0.5 to about 500 W.

RF energy delivered during a time of 1 millisecond to 3 seconds.

The invention claimed is:

1. Apparatus for tissue treatment comprising:
a central blunt urethra fixator, which is a return electrode;
an array of electrodes positioned circumferentially about said central blunt urethra fixator and distanced radially from said central blunt urethra fixator, at least one of said electrodes being an active electrode, and wherein said central blunt urethra fixator and said electrodes protrude from a housing, said central blunt urethra fixator and said electrodes being straight and parallel to each other along their entire lengths; and
a main unit comprising an RF generator, a controller unit, a power supply and a user interface, said main unit configured to deliver RF energy between said return electrode and a conductive tip of said active electrode to create collagen contraction in a vicinity of said active electrode.

2. The apparatus according to claim 1, wherein said central blunt urethra fixator protrudes further out of said housing than said array of electrodes.

3. A method for tissue treatment comprising using the apparatus of claim 1 and:
inserting said central blunt urethra fixator into a urethra of a patient;
inserting said array of electrodes into tissue near said urethra; and
applying RF energy between said active electrode and said return electrode to create collagen contraction in a vicinity of said active electrode to contract collagenous tissue near the urethra.

* * * * *